US00PP28230P3

(12) United States Plant Patent
Olesen

(10) Patent No.: US PP28,230 P3
(45) Date of Patent: Aug. 1, 2017

(54) COMPACT FLORIBUNDA ROSE PLANT NAMED 'POULCAS046'

(50) Latin Name: ***Rosa* hybrid**
Varietal Denomination: Poulcas046

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 12 days.

(21) Appl. No.: 14/756,275

(22) Filed: Aug. 20, 2015

(65) Prior Publication Data

US 2017/0055408 P1 Feb. 23, 2017

(51) Int. Cl.
*A01H 5/02* (2006.01)

(52) U.S. Cl.
USPC ..... Plt./151

(58) Field of Classification Search
USPC ..... Plt./141, 151
See application file for complete search history.

(56) References Cited

PUBLICATIONS

Poulsen Roser A/S "Castle-Perfection by Poulsen" Oct. 2012 (1 page).*

* cited by examiner

*Primary Examiner* — Susan McCormick Ewoldt

(57) ABSTRACT

A new garden rose plant of the Compact Floribunda class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas046'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poulcas046', originated as a single seedling from the stated cross.

The new variety may be distinguished from its male pollen parent and female seed parent primarily by the following characteristics. The female seed parent has medium red flowers, while the new variety has dark red flowers. The male pollen parent is 100 cm in height, while the new variety is 60 cm in height.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas046' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulcas046' was selected in the spring of 2007 by the inventor as a single plant from the progeny of the aforementioned hybridization.

Asexual reproduction of 'Poulcas046' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulcas046' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas046'.

Specifically illustrated in FIG. 1 of the drawings are open flowers, flower petals detached, and the flower in parts.

Figure 1:
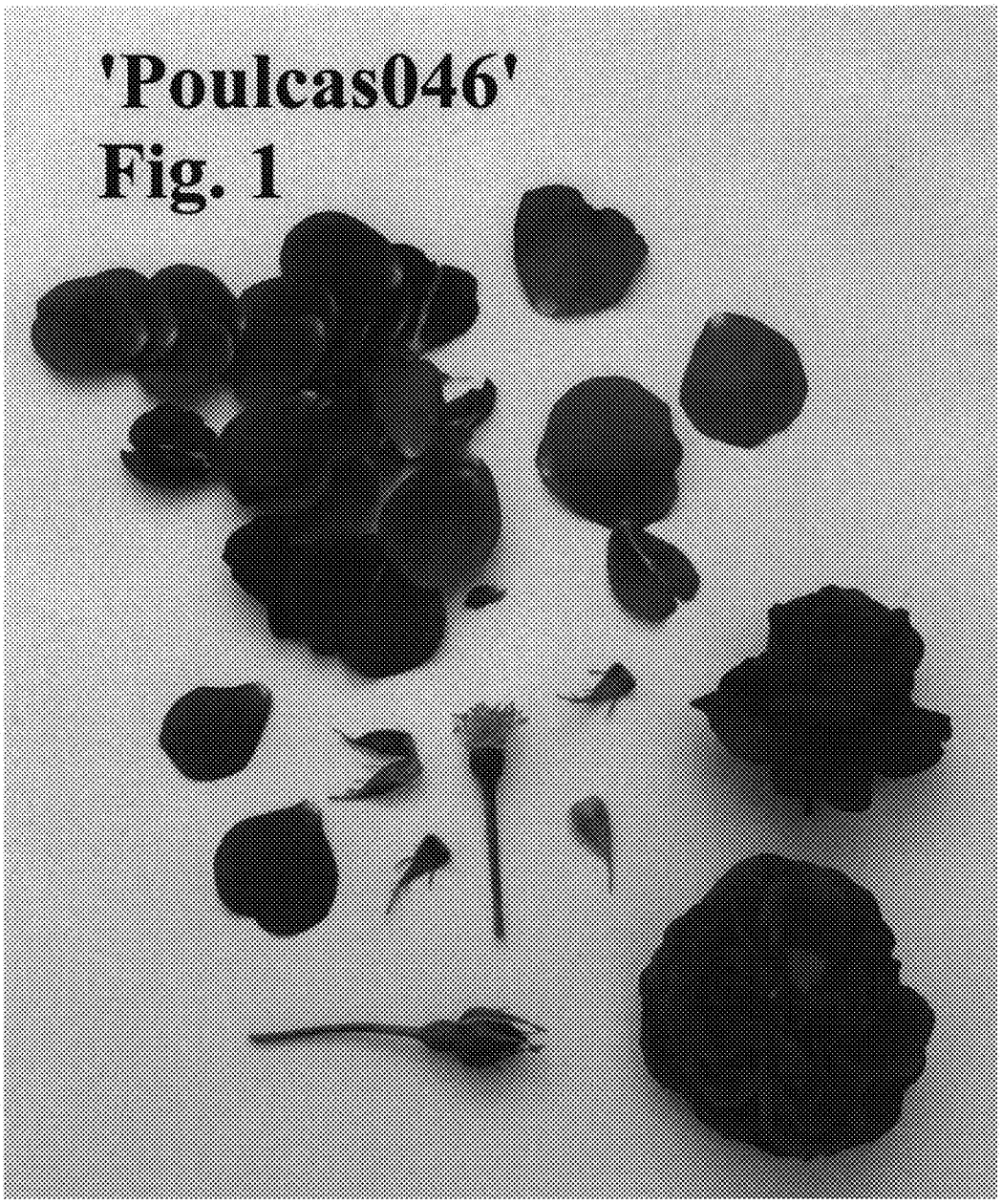
Figure 2:
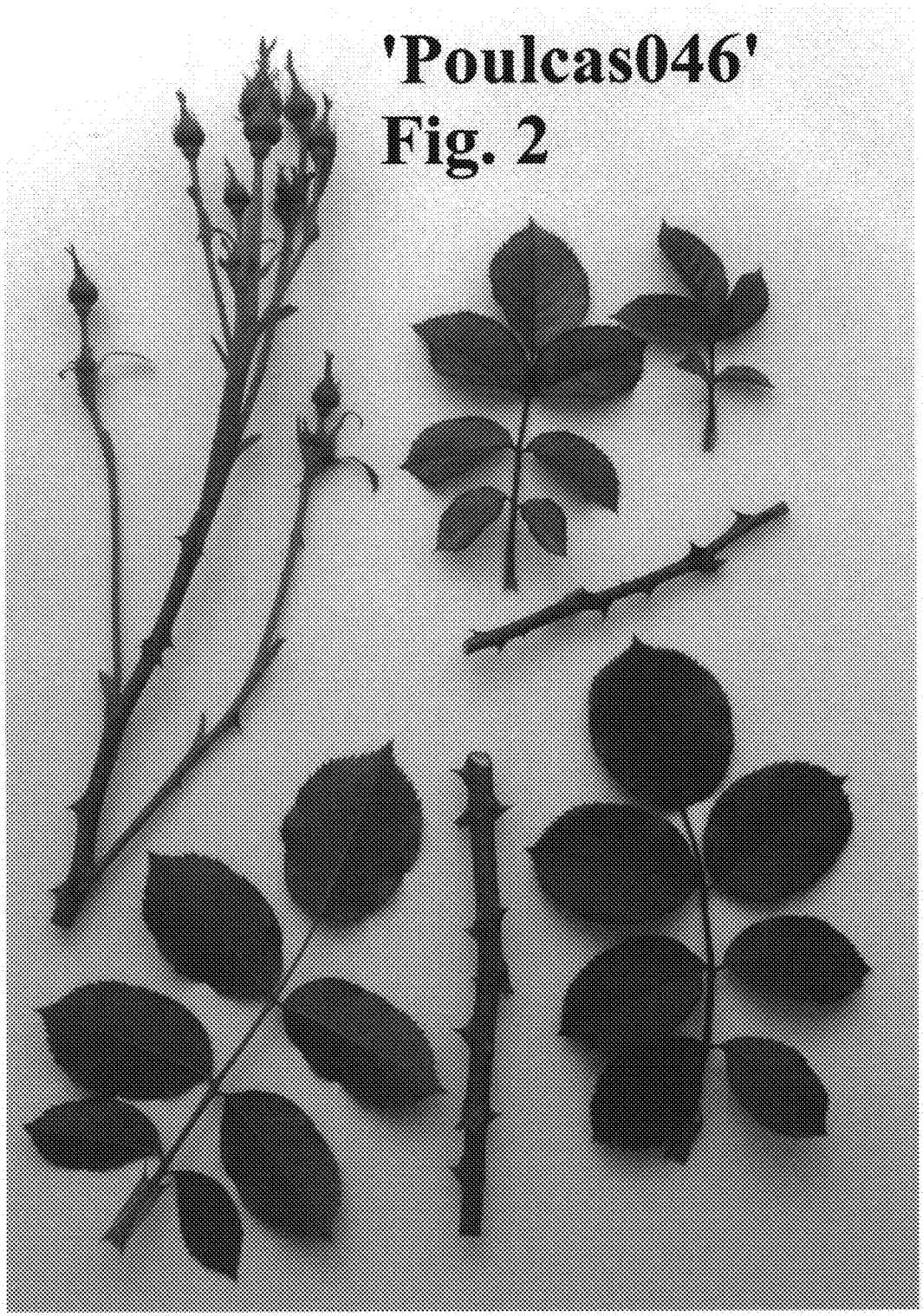

Specifically illustrated in FIG. 2 of the drawings are juvenile and mature leaves, stems, as well as a cluster of flower buds on a flowering branch. Plants shown are 2 years of age.

DETAILED DESCRIPTION OF THE VARIETY

The following is a description of 'Poulcas046',as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas034', U.S. Plant Pat. No. 24,225 are compared to 'Poulcas046' in Chart 1.

CHART 1

| | 'Poulcas046' | 'Poulcas034' |
|---|---|---|
| Petal Count | 45 | 70 |
| Flower Diameter | 65 to 75 mm | 90 to 100 mm |
| General Tonality of Flower Color | Red Group 46A | Red Group 45B |

Flower and Flower Bud

Blooming habit: Continuous.

Flower bud:

*Size*.—Upon opening, 25 mm in length from base of receptacle to end of bud. Bud diameter is 13 mm.

*Bud form*.—Urceolate.

*Bud color*.—As sepals divide petals are Greyed-Purple Group 183A.

*Sepal inner surface*.—Color: Yellow-Green Group 145B with moderate intonations of Greyed-Red Group 182B. Surface: Pubescent.

*Sepal outer surface*.—Color: Yellow-Green Group 144A with intonations of Greyed-Purple Group 183A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—25 mm long, 7 mm wide.

*Receptacle*.—Texture: Smooth. Size: 8 mm in height, 7 mm wide. Color: Yellow-Green Group 144A with weak intonations of Greyed-Purple Group 183A. Shape: Campanulate to elliptical.

*Pedicel*.—Surface: Smooth with a few stipitate glands. Length: About 40 mm. Diameter: 2 mm on average. Color: Yellow-Green Group 145A with light intonations of Greyed-Red Group 182A. Strength: Weak.

*Peduncle*.—Length: 50 to 70 cm. Diameter: About 3.5 mm. Color: Yellow-Green Group 144A. Texture: Smooth.

Flower bud development: Flower buds are borne in panicles of 13 to 15 flower buds per stem. Panicles are about 20 cm in diameter.

Flower bloom:

*Fragrance*.—Light, old rose scent. Duration: The blooms have a duration on the plant of approximately 10 days. Petals fall cleanly away from plant after flowers have fully matured.

*Size*.—Flower diameter is 65 to 75 mm when open. Flower depth is 40 mm.

*Flower shape*.—Double, quartered-rosette with many overlapping petals packed into quarter sections.

*Shape of flower, side view*.—The upper portion is a flattened convex. The lower portion is concave.

Petalage: Under normal conditions, flowers have 45 petals total, 10 of which are petaloids.

General tonality of flower: Open flowers are Red Group 46A.

Petal color:

*Upon opening, outer petals*.—Upper surface: Red Group 46A. Lower surface: Red Group 53B with occasional streaks of White Group N155A.

*Upon opening, inner petals*.—Upper surface: Red Group 46A. Lower surface: Red Group 53B with occasional streaks of White Group N155A.

*Basal petal spots, upon opening*.—Upper surface: Yellow Group 8B. Lower surface: Yellow Group 8B.

*After opening, outer & inner petals*.—Upper surface: Red Group 46A. Lower surface: Red-Purple Group 58A with occasional streaks of White Group N155A.

*Basal petal spots, after opening*.—Upper surface: Yellow Group 8B. Lower surface: Yellow Group 8B.

Petals:

*Petal reflex*.—Somewhat reflexed.

*Margin*.—Entire and uniform. Moderate undulations.

*Shape*.—Generally broad elliptical. Apex shape: Rounded. Base shape: Acute.

*Size*.—About 35 mm (l)×30 mm (w).

*Texture*.—Smooth.

*Thickness*.—Average.

Petaloids:

*Size*.—About 23 mm (l) by 11 mm (w).

*Quantity*.—On average, 10.

*Shape*.—The base is very acute, while the apex is acute or rounded. General shape is irregular.

*Color*.—Upper surface of petaloids are Red Group 46A. Underneath Red-Purple Group 58A with occasional streaks of White Group N155A. The base of petaloids is Yellow Group 8A.

Reproductive flower parts:

*Pollen*.—None observed.

*Anthers*.—Size: 2 mm in length. Color: Yellow-Orange Group 22A. Quantity: 40 on average.

*Filaments*.—Color: Yellow-Orange Group 22A and Yellow Group 12A. Length: 6 mm.

*Pistils*.—Length: 6 mm. Quantity: 25 on average.

*Stigmas*.—Color: Yellow Group 11D.

*Styles*.—Color: Yellow-Green Group 149D.

*Location of stigmas*.—Level in location relative to the length of the filaments and the height of the anthers.

*Hips*.—None observed to date.

Plant

Plant growth: Upright, bushy. Plants are 60 cm in height, and 50 cm wide.

Stems:

*Color*.—Juvenile growth: Yellow-Green Group 144A with Greyed-Purple Group 183A. Mature growth: Yellow-Green Group 144A.

*Length*.—On average, canes are 30 cm from the base of the plant to the flowering portion.

*Diameter*.—About 7 mm.

*Internodes*.—On mature canes about 50 mm between nodes.

*Surface texture*.—Young wood: Smooth. Older wood: Smooth.

Long prickles:

*Incidence*.—12 prickles per 10 cm of stem.

*Size*.—Average length of prickles on mature stems is 8 mm.

*Shape*.—Upper portion is linear. Lower portion is concave.

*Color*.—Juvenile prickles: Greyed-Purple Group 187A. Mature prickles: Yellow-Green Group 146B and Greyed-Purple Group 184A.

Plant foliage:

*Compound leaf*.—About 175 mm (l)×95 (w).

*Quantity*.—2 leaves per 10 cm of stem on average.

*Color of juvenile foliage*.—Upper & lower side: Yellow-Green Group 146C with intonations of Greyed-Purple Group 183C.

*Color of mature foliage*.—Upper side: Yellow-Green Group 147A. Lower side: Yellow-Green Group 147C.

Plant leaves and leaflets:

*Stipules*.—Size: 20 mm long, 10 mm wide. Quantity: 2 per compound leaf. Shape: Linear, slightly broad based with outward extending apices. Margins: Finely serrated with stipitate glands. Color: Yellow-Green Group 146B.

*Petiole*.—Length: About 25 mm. Diameter: 2 mm.

*Upper surface*.—Color: Yellow-Green Group 145B with intonations of Greyed-Purple Group 183B.

*Lower surface*.—Color: Yellow-Green Group 144A.

*Rachis*.—Length: About 90 mm. Upper surface: Color: Greyed-Purple Group 183B.

*Lower surface*.—Color: Yellow-Green Group 144A. Observations: Small prickles

*Leaflet*.—Quantity: Normally 7 leaflets. Margins: Serrated. Size: On average terminal leaflets are 55 mm long, 45 mm wide. Shape: Generally elliptical. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulcas046', substantially as illustrated and described herein, due to its abundant red flowers, disease resistance, and extended period of bloom.

* * * * *

'Poulcas046'

'Poulcas046'